United States Patent [19]

Tenud

[11] 4,190,585
[45] Feb. 26, 1980

[54] PROCESS FOR THE PRODUCTION OF INDOLYL LACTIC ACID

[75] Inventor: Leander Tenud, Visp, Switzerland

[73] Assignee: Lonza Ltd., Basel, Switzerland

[21] Appl. No.: 505,566

[22] Filed: Sep. 13, 1974

[30] Foreign Application Priority Data

Sep. 13, 1973 [CH] Switzerland ............. 13171/73

[51] Int. Cl.$^2$ ............. C07D 307/22; C07D 209/218
[52] U.S. Cl. ............. 260/326.13 R; 260/347.3
[58] Field of Search ............. 260/326, 13 R

[56] References Cited

PUBLICATIONS

Houlihan, "Indoles," Part 1, pp. 246–247 and 208–209 (1972).

Boberg et al., "Annalen Der Chemie", vol. 655, pp. 110–113 (1962).

Robinson et al., "Can. Jour. Chem.", vol. 35, pp. 1578–1581 (1957).

Robinson et al., "J. Chem. Soc.", 1932, p. 302.

*Primary Examiner*—Alton D. Rollins
*Assistant Examiner*—D. B. Springer
*Attorney, Agent, or Firm*—Fisher, Christen & Sabol

[57] ABSTRACT

A process for the production of indolyl lactic acid which includes heating an aqueous solution of 2,3-dihydro-2,5-furan dicarboxylic acid to boiling. The aqueous solution is cooled and reacted with phenyl hydrazine or a salt of phenyl hydrazine. The resultant phenylhydrazone is converted by heating with sulfuric acid to indolyl lactic acid.

14 Claims, No Drawings

PROCESS FOR THE PRODUCTION OF INDOLYL LACTIC ACID

BACKGROUND OF THIS INVENTION

1. Field of this Invention

This invention relates to a novel process for the production of indolyl lactic acid.

2. Prior Art

It is known that indolyl lactic acid can be used as a substitute for trytophane. The synthesis of indolyl lactic acid from very expensive indole pyruvic acid or from gramine and acetoxy malonic ester has however heretofore been economically prohibitive. So even at the present tune, indolyl lactic acid is a product which is produced only in very small quantities.

L- Tryptophan or 2-amino-3-indolylpropanoic acid is a nutrient or essential amino acid.

BROAD DESCRIPTION OF THIS INVENTION

An object of this invention is to produce indolyl lactic acid by a simple and reasonably inexpensive method in order to make available an economical trytophane substitute in relatively large quantities. Other objects and advantages of this invention are set out below or are obvious to one ordinarily skilled in the art from the disclosure of this invention.

This invention involves a process for the production of indolyl lactic acid. The process includes heating an aqueous solution of 2,3-dihydro-2,5-furan dicarboxylic acid to boiling, cooling the aqueous solution, reacting the aqueous solution with phenyl hydrazine or a salt of phenylhydrazine, and converting the resulting phenylhydrazone by heating with sulfuric acid to indolyl lactic acid.

DETAILED DESCRIPTION OF THIS INVENTION

The starting product, namely, 2,3-dihydro-2,5-furan dicarboxylic acid can be produced by an convenient method. One by hydrogenation of, for example, the alkali salt of the 2,5-furan dicarboxylic acid (preferably) hydrogenating with sodium amalgam, and subsequent regrouping of the primarily formed 2,5-dihydro-2,5-furan dicarboxylic acid by boiling of its alkaline solution into the desired 2,3-dihydro-2,5-furan dicarboxylic acid.

2,3-Dihydro-2,5-furan dicarboxylic acid is:

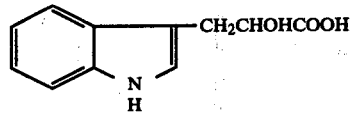

The 2,3-dihydro-2,5-furan dicarboxylic acid is placed in the form of an aqueous solution for the reaction with phenylhydrazine hydrochloride. While the concentration plays no decisive role, preferably 2 to 10 moles of 2,3-dihydro-2,5-furan dicarboxylic acid is used.

The aqueous solution is heated to boiling and is usually kept there for about ½ to 2 hours (preferably 50 to 70 minutes) at the boiling temperature. The solution is then cooled to a temperature between 15° and 100° C. The cooled solution is then reacted with phenyl hydrazine or salt thereof, say for about 10 to about 20 hours. The solution, after cooling, is preferably added to an aqueous phenyl hydrazine hydrochloride solution and left standing for a short period of time while being stirred. The reaction can be conducted at ambient temperature, or more widely, temperatures between 15° to 100° C. can be used. The phenylhydrazine or salt thereof is used in stoichiometric quantities or can be used at a small or slight excess. The phenylhydrazine, or salt thereof, is preferably used in the form of an aqueous solution. The reaction is preferably conducted for 2 to 20 hours.

Any suitable HM (where M is an anion) salt of phenylhydrazine can be used. Preferably water soluble salts of phenylhydrazine is used. More preferably a HX (where X is chlorine, bromine, iodine, fluorine or bisulfate) salt of phenylhydrazine, and most preferably phenylhydrazine hydrochloride is used because it is extremely soluble in water.

After the reaction, the reaction mixture is preferably cooled (preferably in an ice bath) and the precipitated bright yellow crystals filtered out, washed with water and dried.

The phenylhydrazone of the α-keto-α'-hydroxy adipic acid obtained thus is preferably mixed with 8 to 15 percent sulfuric acid and is heated to a temperature of 100° to 150° C. The desired indolyl lactic acid results from that step which involves formation of the indolyl ring and simultaneous decarboxylization.

This ring formation can also be carried out under slightly increased pressure of 3 to 5 atm., whereby the reaction time is reduced to 2 hours. The temperature used in such case is around 130° to 140° C.

To recap, this invention includes dissolving 2,3-dihydro-2,5-furan dicarboxylic acid in water and heating it to boiling temperature, reacting the solution, after cooling, with phenyl-hydrazine, preferably with its hydrochloride, and by converting the developing phenylhydrazone by heating with sulfuric acid into indolyl lactic acid.

Indolyl lactic acid is:

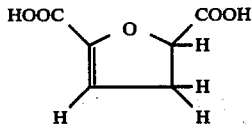

As used in the examples and elsewhere in this application, all percentages, parts, ratios and proportions are on a weight basis unless otherwise stated or obvious to one ordinarily skilled in the art.

EXAMPLE 1

9.42 gm. of 2,3-dihydro-2,5-furan dicarboxylic acid (melting point: 181° to 183° C.) were dissolved in 60 ml of distilled water, which were being heated, and were boiled for one hour under the reflux. The resultant colorless solution was cooled and added to 8.43 gm. of phenylhydrazine hydrochloride in a round-bottomed flask. The reaction mixture was stirred for 15 hours at ambient temperature. Then the reaction mixture was cooled for one hour in an ice bath—the resultant yellowish crystals were filtered off, washed with cold water and dried under a high vacuum at 46° C. 14.42 gm of the phenylhydrazine of α-keto-α'-hydroxyadipic acid resulted. The phenylhydrazone was of bright yellow color and had a melting point of 145° to 148° C. The yield was 93.0 percent, based on the starting 2,3-dihydro-2,5-furan dicarboxylic acid. The phenylhydrazone was recrystallized from ethanol (it can be recrystallized from ethylacetate or water). The recrystallized phenylhydrazone had a melting point of 147° to 148.5° C. The yield after purification was 84.7 percent. The constitution of the phenylhydrazone was proven by means of IR and NMR spectrum analyses. An elemental analysis of the product was:

|  | C | H | N |
|---|---|---|---|
| calculated: | 54.13% | 5.2% | 10.5% |
| found | 54.50% | 5.0% | 10.5% |

EXAMPLE 2

20.04 gm of 2,5-furane dicarboxylic acid was dissolved with 14.50 gm of sodium carbonate in 120 ml of water and was treated with 332 gm. of sodium amalgam (3 percent) for 4 hours. The reaction solution was separated from the mercury and filtered, and boiled for 16 hours under reflux. In order to liberate the 2,3-dihydro-2,5-furane dicarboxylic acid from its sodium salt, the solution was brought to a pH of 2.0 with 4 N hydrochloric acid at 0° C. After filtering, the filtrate was heated under reflux for one hour. The filtrate was cooled and added to 18.546 gm. of phenylhydrazine hydrochloride. The pH dropped to 0.3. The mixture was stirred for 10 hours, cooled in the ice bath, filtered and the crystals were washed in cold water.

From the aqueous phase, 1.89 gm. of phenylhydrazine hydrochloride were recaptured. The yellowish raw product (the phenylhydrozone of α-keto-α'-hydroxy adipic acid) had a melting point of 145° to 147° C. The content was 99.7 percent (pot. titration). The raw phenylhydrazone product produced was recrystallized from aqueous ethanol and 24.655 gm. of pure material having a melting point of 145.5° to 147° C. was obtained. The yield was 74.4 percent, based on the starting 2,5-furan dicarboxylic acid.

EXAMPLE 3

In a 250 ml round flask with reflux condenser, 5.215 gm. of the phenylhydrazone were produced by the method of Example 1 were introduced into and mixed with 200 ml of 10 percent sulfuric acid. After 17.5 hours of boiling under reflux, the mixture was extracted with 1000 ml of ether in three operations. The ether phase was dried over $Na_2SO_4$ and vaporized until dry—the residue was dried at 40° C. under high vacuum. There resulted 3.682 gm. of raw product having a bright yellow color and a melting point of 140° to 142° C. This corresponded to a raw yield of 91.6 percent.

After recrystallization from toluene/water (alcohol/water can be used instead), colorless crystals having a melting point of 145° to 146° C. were obtained. There was a 78.7 percent yield, based on the phenylhydrazone used. An elemental analysis of the indolyl lactic acid was:

|  | C | H | N |
|---|---|---|---|
| Calculated: | 64.38% | 5.10% | 6.83% |
| Found | 64.00% | 5.10% | 6.5% | the IR and NMR spectra were those of the indolyl lactic acid.

EXAMPLE 4

Example 3 was repeated using the phenylhydrazone produced by the method of Example 2.

What is claimed is:

1. The process for the production of indolyl lactic acid which comprises: (i) heating an aqueous solution of 2,3-dihydro-2,5-furan dicarboxylic acid to boiling, (ii) reacting the aqueous solution with phenyl hydrazine or a water soluble HX salt of phenyl hydrazine, wherein X is chlorine, bromine, iodine, fluorine or bisulfate, and (iii) converting the resulting phenylhydrazone by heating from 100° to 150° C. with an aqueous solution containing 8 to 15 percent of sulfuric acid to indolyl lactic acid.

2. The process of claim 1 wherein 2 to 10 moles of water per mole of 2,3-dihydro-2,5-furan dicarboxylic acid is contained in the aqueous solution (i).

3. The process of claim 1 wherein the aqueous solution (i) is heated to boiling and kept at the boiling temperature for ½ to 2 hours.

4. The process of claim 1 wherein the aqueous solution (i) is heated to boiling and kept at the boiling temperature for 50 to 70 minutes.

5. The process of claim 1 wherein the aqueous solution (i), after the boiling step, is cooled to a temperature between 15° and 100° C.

6. The process of claim 1 wherein the phenylhydrazine, or salt thereof, is used in the stoichiometric quantity.

7. The process of claim 1 wherein the phenyldrazine, or salt thereof, is used in an amount which is a slight excess of the stoichiometric quantity.

8. The process of claim 1 wherein the salt of phenylhydrazine is phenylhydrazine hydrochloride.

9. The process of claim 1 wherein the reaction (ii) is with phenyl hydrazine hydrochloride, the cooled aqueous solution being added to an aqueous solution of the phenyl hydrazine hydrochloride and the combination being allowed to stand with stirring for a short period of time.

10. The process of claim 1 wherein the reaction (ii) with phenylhydrazine, or salt thereof, is conducted at a temperature between 15° and 100° C.

11. The process of claim 10 wherein the reaction (ii) is conducted at ambient temperature.

12. The process of claim 1 wherein the reaction (ii) with phenylhydrazine, or salt thereof, is conducted for about 10 to about 20 hours.

13. The process of claim 1 wherein the reaction mixture from the reaction with phenylhydrazine, or salt thereof, is cooled and the resultant phenylhydrazone crystals are removed from the reaction mixture, washed with water and dried.

14. The process of claim 1 wherein the phenylhydrazone conversion step (iii) is conducted at a pressure of 3 to 5 atmospheres and at a temperature between 130° and 140° C.

* * * * *